United States Patent
Maurer et al.

(10) Patent No.: US 11,511,132 B2
(45) Date of Patent: *Nov. 29, 2022

(54) TUMOR TRACKING DURING RADIATION TREATMENT USING ULTRASOUND IMAGING

(71) Applicant: Accuray Incorporated, Sunnyvale, CA (US)

(72) Inventors: Calvin R. Maurer, San Jose, CA (US); Jay West, Mountain View, CA (US); Petr Jordan, Redwood City, CA (US)

(73) Assignee: Accuray Incorporated, Sunnyvale, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 16/910,998

(22) Filed: Jun. 24, 2020

(65) Prior Publication Data

US 2020/0316403 A1 Oct. 8, 2020

Related U.S. Application Data

(60) Continuation of application No. 14/800,473, filed on Jul. 15, 2015, now Pat. No. 10,702,712, which is a
(Continued)

(51) Int. Cl.
*A61N 5/10* (2006.01)
*A61B 8/08* (2006.01)
(Continued)

(52) U.S. Cl.
CPC ............ *A61N 5/1049* (2013.01); *A61B 5/055* (2013.01); *A61B 6/032* (2013.01); *A61B 6/4458* (2013.01);
(Continued)

(58) Field of Classification Search
CPC .. A61N 5/1049; A61N 5/1039; A61N 5/1045; A61N 5/107; A61N 5/1077;
(Continued)

(56) References Cited

U.S. PATENT DOCUMENTS 5,411,026 A 5/1995 Carol
5,447,154 A 9/1995 Cinquin et al.
(Continued)

FOREIGN PATENT DOCUMENTS

WO 2007021420 2/2007

OTHER PUBLICATIONS

International Search Report for PCT/US2011/046853 dated Oct. 18, 2011, 6 pgs.
(Continued)

*Primary Examiner* — Peter Luong
(74) *Attorney, Agent, or Firm* — Womble Bond Dickinson (US) LLP (57) ABSTRACT

Systems and methods for tracking a target volume, e.g., tumor, in real-time during radiation treatment are provided. The system includes a memory to store a pre-acquired 3D image of the anatomy of interest in a first reference frame and a processor, operative coupled with the memory, to receive, from an ultrasound probe, a set-up ultrasound image of the anatomy of interest in a second reference frame. The processor further to establish a transformation between the first and second reference frames by registering the set-up ultrasound image with the pre-acquired 3D image and receive, from the ultrasound probe, an intrafraction ultrasound image of the anatomy of interest. The processor further to register the intrafraction ultrasound image with the set-up ultrasound image and track motion of the anatomy of interest based on the registered intrafraction ultrasound image.

25 Claims, 6 Drawing Sheets

Related U.S. Application Data division of application No. 13/204,559, filed on Aug. 5, 2011, now Pat. No. 9,108,048.

(60) Provisional application No. 61/371,596, filed on Aug. 6, 2010.

(51) Int. Cl.

| | | |
|---|---|---|
| *A61B 8/00* | (2006.01) | |
| *A61B 6/03* | (2006.01) | |
| *A61B 5/055* | (2006.01) | |
| *A61B 6/00* | (2006.01) | |
| *A61B 90/00* | (2016.01) | |
| *A61B 6/02* | (2006.01) | |
| *A61B 6/04* | (2006.01) | |

(52) U.S. Cl.
CPC .............. *A61B 6/5247* (2013.01); *A61B 8/08* (2013.01); *A61B 8/085* (2013.01); *A61B 8/4245* (2013.01); *A61B 8/4263* (2013.01); *A61B 8/4416* (2013.01); *A61B 8/4444* (2013.01); *A61B 8/483* (2013.01); *A61B 8/5238* (2013.01); *A61B 8/5261* (2013.01); *A61B 90/39* (2016.02); *A61N 5/107* (2013.01); *A61N 5/1039* (2013.01); *A61N 5/1045* (2013.01); *A61N 5/1077* (2013.01); *A61N 5/1081* (2013.01); *A61N 5/1083* (2013.01); *A61B 6/022* (2013.01); *A61B 6/0487* (2020.08); *A61B 6/4417* (2013.01); *A61B 8/4218* (2013.01); *A61B 2090/3995* (2016.02); *A61N 5/1067* (2013.01); *A61N 2005/1054* (2013.01); *A61N 2005/1055* (2013.01); *A61N 2005/1058* (2013.01); *A61N 2005/1061* (2013.01); *A61N 2005/1062* (2013.01)

(58) Field of Classification Search
CPC .. A61N 5/1081; A61N 5/1083; A61N 5/1067; A61N 5/055; A61N 6/032; A61N 6/4458; A61N 6/5247; A61N 6/022; A61N 6/0487; A61N 6/4417; A61N 8/08; A61N 8/4245; A61N 8/4263; A61N 8/4416; A61N 8/4444; A61N 8/483; A61N 8/5238; A61N 8/5261; A61N 8/4218; A61N 90/39; A61N 2009/3995; A61N 2005/1054; A61N 2005/1055; A61N 2005/1058; A61N 2005/1061; A61N 2005/1062

See application file for complete search history.

(56) References Cited

U.S. PATENT DOCUMENTS

| | | |
|---|---|---|
| 5,622,187 A | 4/1997 | Carol |
| 5,672,877 A | 9/1997 | Liebig et al. |
| 5,954,647 A | 9/1999 | Bova et al. |
| 6,019,724 A | 2/2000 | Gronningsaeter et al. |
| 6,325,758 B1 | 12/2001 | Carol et al. |
| 6,546,279 B1 | 4/2003 | Bova et al. |
| 6,560,354 B1 | 5/2003 | Mauer, Jr. et al. |
| 6,961,405 B2 | 11/2005 | Scherch |
| 7,289,227 B2 | 10/2007 | Smetak et al. |
| 7,535,411 B2 | 5/2009 | Falco |
| 7,634,304 B2 | 12/2009 | Falco et al. |
| 7,662,097 B2 | 2/2010 | Falco et al. |
| 7,672,705 B2 | 3/2010 | Lachaine et al. |
| 2004/0034301 A1 | 2/2004 | Falco |
| 2005/0180544 A1 | 8/2005 | Sauer et al. |
| 2006/0074292 A1 | 4/2006 | Thomson et al. |
| 2007/0003123 A1 | 1/2007 | Fu et al. |
| 2007/0015991 A1 | 1/2007 | Fu et al. |
| 2007/0038058 A1 | 2/2007 | West et al. |
| 2007/0286342 A1 | 12/2007 | Fuller |
| 2008/0008369 A1 | 1/2008 | Koptenko et al. |
| 2008/0119725 A1 | 5/2008 | Lloyd |
| 2008/0177279 A1 | 7/2008 | Sumanaweera et al. |
| 2008/0219540 A1 | 9/2008 | Ter Mors |
| 2009/0304252 A1 | 12/2009 | Hyun et al. |
| 2010/0069920 A1 | 3/2010 | Naylor et al. |
| 2011/0009742 A1 | 1/2011 | Lachaine et al. |

OTHER PUBLICATIONS

Kilby et al., "The CyberKnife® Robotic Radiosurgery System in 2010", Tech. in Cancer Res. and Treatment vol. 9, No. 5, pp. 433-452 (2010).

Lee et al., "Sensorless and real-time registration between 2D ultrasound and preoperative images of the liver", IEEE Int. Symposiun Apr. 14, 2010 pp. 388-391.

Meeks et al., "Ultrasound-guided extracranial radiosurgery: Technique and application", Int. J. Radiation Oncology Biol. Phys. vol. 55, No. 4, pp. 1092-1101 (2003).

Wang et al., "3D Ultrasound-based Patient Positioning for Radiotherapy", Proc. of SPIE vol. 6141, K1-K9 (2006).

TUMOR TRACKING DURING RADIATION TREATMENT USING ULTRASOUND IMAGING

RELATED APPLICATIONS

The application is a continuation of U.S. patent application Ser. No. 14/800,473, filed Jul. 15, 2015, which is a divisional of U.S. patent application Ser. No. 13/204,559, filed Aug. 5, 2011, issued on Aug. 18, 2015 as U.S. Pat. No. 9,108,048, which claims priority to U.S. Provisional Application No. 61/371,596 filed Aug. 6, 2010, which are hereby incorporated by reference in its entirety.

FIELD

This application relates to systems and methods for locating and tracking an anatomy of interest during radiation treatment using ultrasound imaging.

DISCUSSION OF RELATED ART

External beam radiation therapy is one of the available non-invasive methods to treat a pathological anatomy (e.g., tumor, lesion, vascular malformation, nerve disorder, etc.). In one type of external beam radiation therapy, an external radiation source directs a sequence of x-ray beams at a target volume, e.g., a tumor, from multiple angles, with the patient positioned so the target volume is at the center of rotation (isocenter) of the beam. As the angle of the radiation source changes, every beam passes through the target volume, but passes through a different area of healthy tissue on its way to and from the target volume. As a result, the cumulative radiation dose at the target volume is relatively high, and the average radiation dose to healthy tissue is relatively low.

The term "radiosurgery" refers to an external beam radiation therapy procedure in which radiation is applied to a target volume at levels that are sufficient to necrotize a pathology. Radiosurgery is typically characterized by relatively high radiation doses per treatment (e.g., 1000-2000 centiGray), extended treatment times (e.g., 45-60 minutes per treatment), and hypo-fractionation (e.g., one to five days of treatment). The term "radiotherapy" refers to an external beam radiation therapy procedure in which radiation is applied to a target volume in many more fractions than in radiosurgery. Radiotherapy is typically characterized by a lower dose per fraction (e.g., 100-200 centiGray), shorter treatment times (e.g., 10 to 30 minutes per treatment), and hyper-fractionation (e.g., 30 to 45 days of treatment). For convenience, the term "radiation treatment" is used herein to mean radiosurgery and/or radiotherapy, unless otherwise noted.

Image-guided radiation therapy (IGRT) devices include gantry-based systems and robotic-based systems. In gantry-based systems, the radiation source, e.g., a linear accelerator (LINAC), is mounted on a gantry that moves the source around a center of rotation (isocenter) in a single plane. The radiation source may be rigidly attached to the gantry or attached by a gimbaled mechanism. Each time a radiation beam is delivered to a target volume during treatment, the axis of the beam passes through the isocenter. Radiation beam delivery is, therefore, limited by the rotation range of the radiation source mounted on the gantry, the angular range of the gimbaled mechanism (if present), and by the number of degrees of freedom available on a patient positioning system. Additionally, the shape of the radiation can be modified using a multileaf collimator. Alternatively, the treatment system has the radiation source mounted on a robotic arm with at least five degrees of freedom to enable non-coplanar delivery to a target volume. One example of such a system is the CYBERKNIFE® Robotic Radiosurgery System manufactured by Accuray Incorporated. (Sunnyvale, Calif.).

Whatever the radiation treatment delivery system (e.g., gantry or robot mounted radiation source), a physician must first make a diagnosis, and then prepare a treatment plan for delivering radiation to a target volume, such as a diagnosed tumor. Typically, a physician obtains a high-resolution three-dimensional (3D) image of the tumor using computerized tomography (CT), magnetic resonance imaging (MRI), positron emission tomography (PET), ultrasound (US), 3D rotational angiography (3DRA), or other suitable technology. This image may be used for diagnosis, or the diagnosis may have been previously performed using other means (e.g., biopsy). Based on the information about the tumor contained in the 3D image, such as the size, shape, density, and type of tumor, the physician develops a radiation treatment plan. The plan includes, for example, the type of radiation to be applied to the target volume, such as ionizing radiation, e.g., x-rays, gamma rays, or protons, or non-ionizing radiation, e.g., a laser beam. The plan also includes, without limitation, the total dose of radiation to be delivered to the target volume, the dose fractionation, and the direction(s) from which the radiation is to be delivered (for a robotic delivery system) or the shape and angle from which the radiation is to be delivered (for a gantry-based system). Treatment planning systems are commercially available, such as the MULTIPLAN® Treatment Planning System from Accuray Incorporated (Sunnyvale, Calif.) and the ECLIPSE™ system from Varian Medical Systems (Palo Alto, Calif.).

After the plan is developed, the patient is placed in a treatment room that typically contains a radiation source, e.g., an x-ray source, gamma ray source, proton source, or laser source, and a support for the patient, such as a bed or couch on which the patient is to be positioned. Prior to delivering the radiation, the patient is aligned in the treatment room such that the target volume is aligned in the treatment room reference frame in the same manner in which it was aligned in the 3D planning image reference frame. With the patient positioned on the support, one or more "set-up" images are acquired, providing the target position within the treatment room reference frame, for example but not by way of limitation, using a pair of stereoscopic x-ray imagers, a cone beam-CT imager, or x-ray tomosynthesis. The set-up image(s) are registered to reference pre-treatment image(s) (e.g., a planning 3D image or digitally reconstructed radiographs (DRRs) obtained from the planning 3D image) to provide a transformation between the planning image reference frame and the treatment room reference frame. The transformation can be used to adjust radiation delivery during treatment or to adjust the patient support to align the target volume for treatment.

In one example, a stereoscopic pair of two-dimensional (2D) projection images is acquired at the time of patient set-up. The 2D projection images are compared or registered with 2D DRRs derived from the 3D planning image data. A DRR is a synthetic x-ray image generated by casting (mathematically projecting) rays through the 3D planning image data, simulating the geometry and energy of the treatment room x-ray imaging system. The resulting DRRs then have the same scale, point of view, and energy as the treatment room x-ray imaging system, and can be compared or registered with the set-up images to determine the position and orientation of the target volume, as well as the surrounding tissue, within the treatment room frame and relative to the planning image reference frame. The CYBERKNIFE® System (Accuray Incorporated) uses such a system for both patient set-up and intrafraction target tracking.

Figure 1:
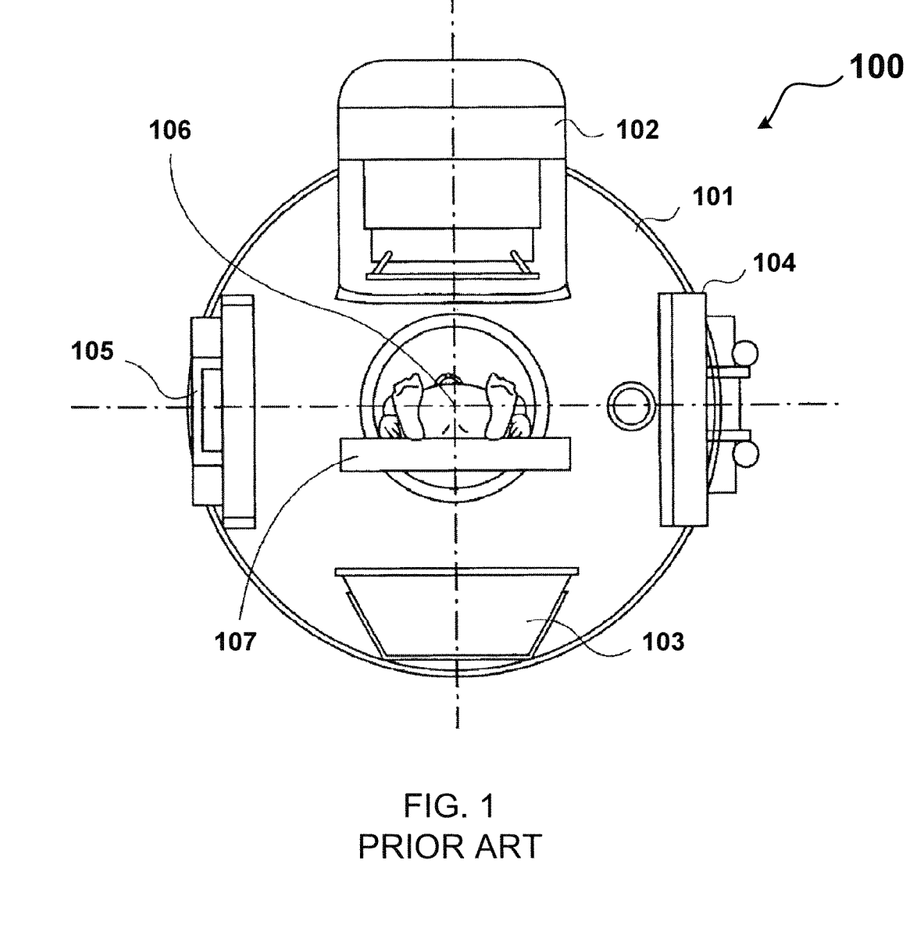
FIG. 1 schematically illustrates a conventional gantry-based radiation treatment system.

In a typical gantry-based treatment system, a 3D cone beam CT set-up image is registered to a 3D planning image, a 3D to 3D registration problem. A cone beam CT image, as is well known, is acquired by obtaining a series of cone beam projection images over a range of gantry angles (typically 180 degrees or more), and the projection image data is back-projected to obtain a CT image. FIG. 1 illustrates a conventional gantry-based IGRT system 100. System 100 includes gantry 101, which includes a megavolt (MV) energy source 102 directed to a MV imager 103 and a kilovolt (kV) X-ray source 104 directed to a kV imager 105. The gantry 101 rotates around an isocenter 106 where a patient on a treatment couch 107 would be located for treatment. Either or both sources 102 and 104 could be used to obtain cone beam projection image data for use in generating a cone beam CT set-up image.

As the treatment plan is executed, the target volume may in some circumstances move relative to its position in the set-up image(s), for example because of patient motion. Such motion can result in detrimental irradiation of otherwise healthy tissue, or over-irradiation of one part of the target volume and under-radiation of another part. Some radiation treatment systems are configured to compensate for at least some movement of the target volume during treatment. For example, the system may periodically acquire additional images of the target volume, e.g., using the same imager as for the set-up images, and compare the additional images to the set-up image(s) as described previously to track intrafraction target motion. Based on the comparison, the system may reposition the radiation source and/or treatment couch so as to account for target volume motion, and thus to deliver radiation more accurately in accordance with the treatment plan. However, in configurations where the additional images are acquired using ionizing radiation sources, it may be dangerous and/or impractical to acquire such images with a frequency sufficient to detect and compensate for patient and/or target movement, especially in cases when the treatment target undergoes respiratory motion, An additional limitation of images created with projection X-rays is that the soft-tissue contrast is not always sufficient to allow the anatomy of interest being tracked to be well visualized.

SUMMARY

Embodiments of the present invention provide systems and methods for real-time tracking using ultrasound imaging of a structure, such as a tumor, during radiation treatment. Specifically, during patient set-up and/or throughout the radiation treatment procedure, an anatomy of interest, e.g. the treatment target, is ultrasonically imaged to track and compensate for motion in real-time. Because such imaging does not involve ionizing radiation, it may safely be performed continuously, or with a frequency that is substantially higher than a frequency with which images could be safely acquired using ionizing radiation. Additionally, ultrasound imaging is particularly well suited to imaging soft tissue, enabling the position and orientation of organs such as the prostate, kidneys, and the like to be monitored. Under some aspects of the present invention, x-ray or other conventional images are also obtained. As described in greater detail below, such images may be used to relate the reference frame of the ultrasound images to the previously obtained 3D treatment planning image. Under one aspect of the present invention, a system for tracking an anatomy of interest comprises an ultrasound probe configured to obtain ultrasound images of the anatomy; an x-ray imager configured to obtain x-ray images of the patient; and a controller in operable communication with the ultrasound probe and the x-ray imager. The controller comprises a processor and a computer-readable medium that stores a pre-acquired 3D image of the patient in a first reference frame, as well as instructions for causing the processor to perform the following functions: instructing the x-ray imager to obtain an x-ray image of the patient in a second reference frame; instructing the ultrasound probe to obtain a set-up ultrasound image of the anatomy of interest substantially simultaneously as the x-ray image is obtained, the set-up ultrasound image being in the second reference frame and inherently registered with the x-ray image; establishing a transformation between the first and second reference frames by registering the pre-acquired 3D image and the x-ray image; instructing the ultrasound probe to obtain an intrafraction ultrasound image of the anatomy of interest, the intrafraction ultrasound image being in the second reference frame; registering the intrafraction ultrasound image with the set-up ultrasound image; and tracking motion of the anatomy of interest based on the registered intrafraction ultrasound image.

Note that the system may include a single controller, a single processor, and a single computer-readable medium storing such instructions. Alternatively, the functionality may be distributed across multiple controllers, processors, and/or computer-readable medium.

In some embodiments, the set-up ultrasound image and the x-ray image each contain information about a plurality of implanted fiducial markers, and the computer-readable medium stores instructions for causing the processor to establish a position and orientation of the ultrasound image based on the information about the fiducial markers.

In other embodiments, the system further comprises markers affixed to the ultrasound probe and a tracking system configured to estimate the position of the markers, e.g., by means of electromagnetic or optical tracking. The computer-readable medium stores instructions for causing the processor to establish a position and orientation of the ultrasound probe in the second reference frame based on the output of the tracking system and to establish a position and orientation of the set-up ultrasound image based on the identified position and orientation.

In still other embodiments, the computer-readable medium stores an atlas image pair consisting of a 3D image of the same type as the pre-treatment 3D image, and a co-registered ultrasound image, and instructions for causing the processor to establish a position and orientation of the set-up ultrasound image by registering the pre-treatment 3D image to the atlas 3D image via a first transformation, registering the x-ray image to the atlas 3D image or the pre-treatment 3D image via a second transformation, registering the set-up ultrasound image to the atlas ultrasound image via a third transformation, and then registering the set-up ultrasound image to at least one of the pre-acquired 3D image and the x-ray image based on the first, second, and third transformations.

In some embodiments, the x-ray imager comprises a stereoscopic pair of x-ray imaging sources configured to irradiate corresponding x-ray detectors. The stereoscopic pair of x-ray imaging sources may be configured to obtain information about the ultrasonic probe in the x-ray image. The computer-readable medium may store instructions for causing the processor to determine the position and orientation of the ultrasound probe based on the information about the probe in the x-ray image.

Some embodiments further include a LINAC configured to irradiate the target volume with a plurality of radiation fractions. The computer-readable medium may store instructions for causing the processor to adjust a position and orientation of the LINAC based on intrafraction target volume motion. Alternatively, or additionally, the computer-readable medium may store instructions for causing the processor to adjust a position and orientation of a patient treatment couch relative to the LINAC based on the identified movement of the target volume.

In some embodiments, the 3D planning image comprises a volumetric CT image, or both a volumetric CT image and MR image.

Under another aspect of the present invention, a method for tracking a target volume comprises: obtaining a pre-acquired 3D image of the target volume in a first reference frame; obtaining an x-ray image and an ultrasound image of the target volume in a second reference frame substantially simultaneously with one another, the set-up ultrasound image being inherently registered with the x-ray image; establishing a transformation between the first and second reference frames by registering the pre-acquired 3D image and the x-ray image; obtaining an intrafraction ultrasound image of the target volume, the intrafraction ultrasound image being in the second reference frame; registering the intrafraction ultrasound image with the set-up ultrasound image; and tracking target volume motion based on the transformed images of the plurality.

In other embodiments, the pre-acquired 3D image of the target volume is obtained in a first reference frame; an X-ray image and an ultrasound image of the target volume are obtained in a second reference frame substantially simultaneously with one another, the set-up ultrasound image being inherently registered with the X-ray image establishing a transformation between the first and second reference frames by registering the pre-acquired 3D image and the x-ray image; obtaining an intrafraction ultrasound image of the target volume after the ultrasound probe has moved, the intrafraction ultrasound image then being in a third reference frame; registering the intrafraction ultrasound image in the third reference frame with the set-up ultrasound image in the second reference frame by means of the output of a tracking system (e.g. optical or electromagnetic) and markers attached to the ultrasound probe; and tracking target volume motion based on the transformed images of the plurality.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Embodiments of the present invention enhance the accuracy of radiation treatment by facilitating the tracking of an anatomy of interest, e.g., a tumor, using ultrasound imaging. Specifically, after a physician plans a patient's radiation treatment using suitable methods (e.g., by obtaining a high-resolution planning image of the target volume and determining the angles, doses, radiation fields, and number of fractions of radiation to be administered to the target volume), the patient is positioned in a treatment room and brought into contact with a suitably positioned ultrasound probe. The position and orientation of the target volume in the treatment room reference frame is approximately aligned with the planning image reference frame during a patient set-up stage, at which time a set-up ultrasound image (preferably a 3D ultrasound image) is obtained. According to the present invention, the set-up ultrasound image is obtained at substantially the same time as a second set-up image using another modality (e.g., cone-beam CT, stereoscopic x-ray, or monoscopic x-ray), and the relation between the coordinate frames of the ultrasound image and the second set-up image are determined, e.g. by means of tracking the ultrasound probe in the treatment room, or by means of visualizing part or all of the ultrasound probe in the second set-up image. Following the set-up procedure, the set-up ultrasound image may be registered with intrafraction ultrasound images for use in tracking target motion in real-time. The treatment plan is then executed based on the actual position and orientation of the target volume, as identified in the intrafraction ultrasound images, which may be registered to the set-up ultrasound image, which are inherently registered with the set-up image obtained by another modality, which may be registered to the planning image. By comparison, direct registration of ultrasound images to images obtained using other modalities (e.g., ultrasound-to-CT, ultrasound-to-MRI, or ultrasound-to-PET) is a relatively time-consuming and difficult problem, as will be appreciated by the skilled artisan. The irradiation of the target volume can then be adjusted accordingly, so as to avoid or reduce the irradiation of otherwise healthy tissue or critical organs as a result of movement of the target volume, and thus to more accurately deliver the treatment plan created by the physician. The use of ultrasound imaging can also enhance the system's ability to track soft tissues that are difficult to visualize using x-ray based imaging, thus enhancing the ability to perform radiation treatment on abdominal structures such as the liver, pancreas, and kidneys; breast tissue; ormale or female pelvic structures such as the prostate, bladder, cervix, or uterus.

First, one embodiment of a radiation treatment system for providing real-time tracking of a target volume using ultrasound imaging will be described. Then, exemplary methods of using such a system during radiation treatment will be described. Lastly, various components of the radiosurgical system will be described in greater detail, and some examples of alternative embodiments will be provided.

Figure 2:
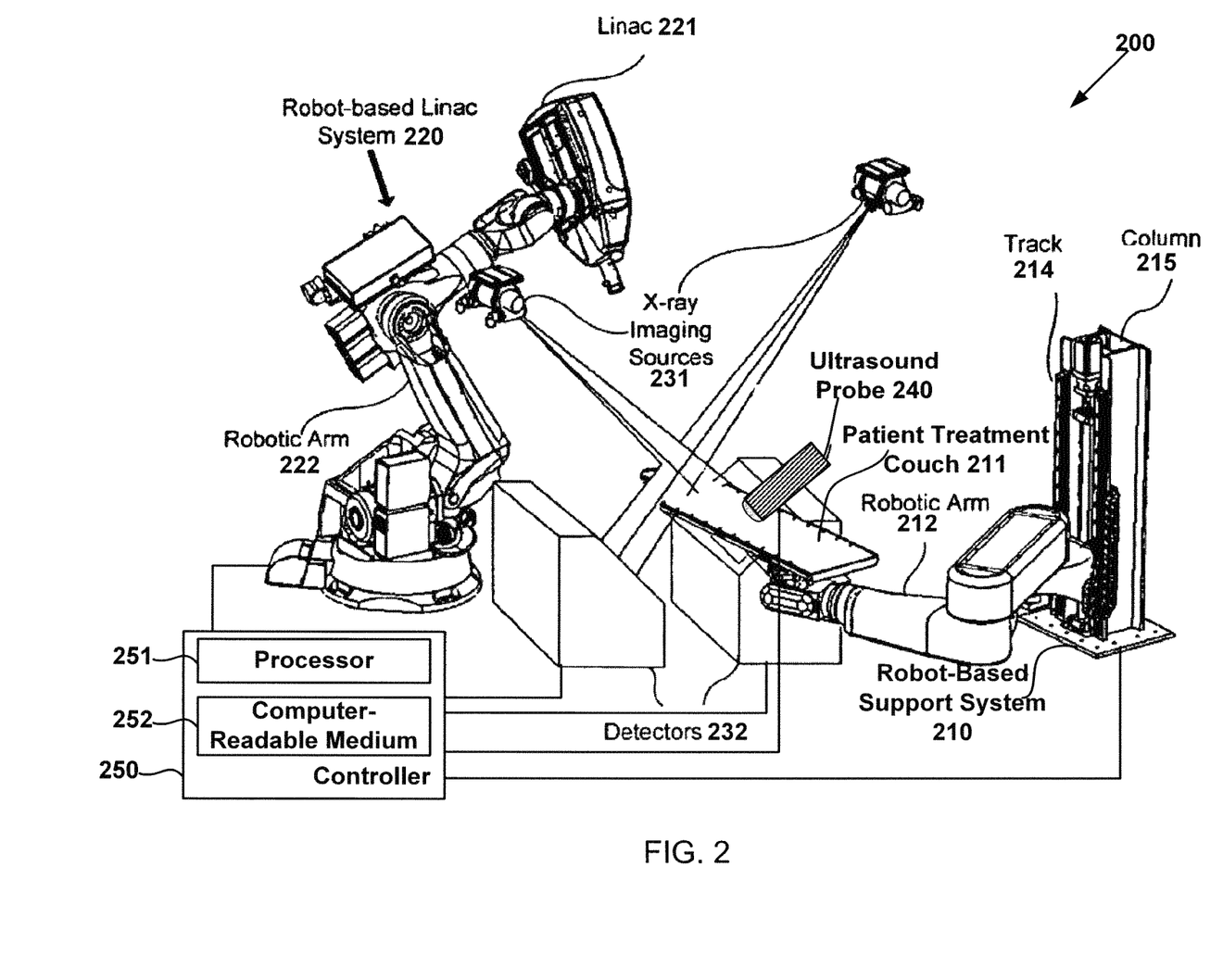
FIG. 2 schematically illustrates a perspective view of a robot-based radiation treatment system having an ultrasound probe for tracking a target volume.

FIG. 2 schematically illustrates a perspective view of a robot-based radiation treatment system, according to some embodiments of the present invention. A gantry-based radiation treatment system is described further below with reference to FIG. 5.

System 200 includes a robot-based support system 210 for supporting and positioning a patient (not illustrated), a robot-based linear accelerator (LINAC) system 220 for irradiating a target volume, such as a tumor, x-ray imaging sources 231 and corresponding detectors 232, ultrasound probe 240, and controller 250. Controller 250 is in operable communication with robot-based support system 210, robot-based LINAC system 220, x-ray imaging sources 231, detectors 232, and ultrasound probe 240, and coordinates the operation of each of these components before and during the radiation treatment by issuing appropriate commands to each component, for example as described in greater detail below.

In the embodiment illustrated in FIG. 2, robot-based support system 210 includes patient treatment couch 211, robotic arm 212, track 214, and column 215. Responsive to instructions from controller 250, robot-based support system 210 moves robotic arm 212 in any suitable direction, e.g., along track 214 and/or column 215, so as to adjust the position and/or orientation of patient treatment couch 211 and thus appropriately position the patient before and/or during the radiation treatment, in accordance with the treatment plan.

Robot-based LINAC system 220 includes LINAC 221 and robotic arm 222. Responsive to instructions from controller 250, robot-based LINAC system 220 moves LINAC 221 to a desired position and orientation using robotic arm 222, and generates radiation of the desired type, energy, field, and dose using LINAC 221, in accordance with the treatment plan. Controller 250 coordinates the movements of robot-based support system 210 to provide appropriate positioning and orientation of the patient relative to the treatment room reference frame, which may be defined to have its origin at an arbitrary point $(x_2, y_2, z_2)$ in the treatment room, both for patient set-up and for intrafraction patient adjustment. For example, controller 250 may instruct robot-based support system 210 to provide coarse (relatively large-scale) movements of the patient, e.g., during patient set-up, to position the subject relatively close to an aligned position (e.g., treatment room reference frame aligned with planning image reference frame) such that the x-ray imaging sources and detectors can complete the set-up procedure as described more thoroughly herein. Or, for example, controller 250 may instruct robot-based LINAC system 212 to provide fine (relatively small-scale) movements of the LINAC 221, e.g., during execution of the treatment plan.

X-ray imaging sources 231 and detectors 232 are configured to obtain x-ray images of the patient or nearby anatomical structures responsive to instructions from controller 250, e.g., at appropriate times before and during the radiation treatment. Each of x-ray imaging sources 231 is arranged at a predetermined angle relative to vertical, e.g., at 45 degrees from vertical, such that x-ray radiation generated by that source passes through the target volume and is received by corresponding detector 232. Based on the received radiation, each of detectors 232 obtains an x-ray image of the target volume. The pair of thus-obtained images may be referred to as "stereoscopic x-ray images," and is provided from detectors 232 to controller 250 for further processing, as described in greater detail below.

Ultrasound probe 240 may be any suitable 1D, 1.5D, 2D, 2.5D, or 3D ultrasound probe, such as one of the commercially available probes mentioned further below. Ultrasound probe 240 preferably is configured to obtain a 3D ultrasound image of the target volume responsive to instructions from controller 250, e.g., at appropriate times before and during the radiation treatment. Ultrasound probe 240 is brought into stable physical contact with the patient using any suitable support structure. For example, in one embodiment, ultrasound probe 240 is coupled to a robotic arm (not illustrated) that is in operable communication with controller 250 and that positions probe 240 responsive to appropriate instructions from controller 250. Alternatively, a fixed structure or arm (e.g., fixed to couch 211) holds ultrasound probe 240 in position. Coupling gel or other suitable ultrasound couplant may be provided between the probe 240 and the patient's skin to enhance the quality of the ultrasound images. As the skilled artisan will appreciate, other configurations are possible. The position of ultrasound probe 240 need not be rigidly fixed within the treatment room, and indeed need not be known before the patient set-up step. Instead, as described in greater detail below, the position of ultrasound probe 240 within the treatment room reference frame may be tracked or otherwise determined at appropriate times before and during the radiation treatment.

Controller 250 includes processor 251 and computer-readable medium 252, each of which may have any suitable structure known in the art. For example, processor 251 may be a conventional computer microprocessor, and computer-readable medium 252 may be any suitable memory, such as a conventional hard drive, ROM, or RAM. Note that although system 200 is primarily described as having a single controller 250 with a single processor 251 and a single computer-readable medium 252, each of these instead may be provided as a plurality of elements distributed in, or even outside of, system 200. For example, one controller may be used to control x-ray image acquisition, another controller to control ultrasound image acquisition, another controller for image registration and transform computation, and so forth. Any suitable arrangement may be used.

As mentioned above, controller 250 coordinates the operation of the different components of system 200. In the illustrated embodiment, such functionality is achieved by storing appropriate instructions in computer-readable medium that, when read by the processor, cause the processor to perform the functions set forth in the instructions. For example, the instructions may cause the processor 251 to instruct robot-based support system 210 to move the patient treatment couch 211 to a suitable location; to instruct robot-based LINAC system 220 to move the LINAC 221 to a suitable location and/or to irradiate the patient with radiation having suitable characteristics; to instruct x-ray imaging sources 231 and detectors 232 to obtain a pair of stereoscopic x-ray images at a suitable time; and/or to instruct ultrasound probe 240 to obtain a 3D ultrasound image at a suitable time. As described in greater detail below with reference to FIGS. 3 and 4, the particular instructions stored in medium 252 may be based, at least in part, on the treatment plan prepared by the physician for treating the particular target volume.

Figure 3:
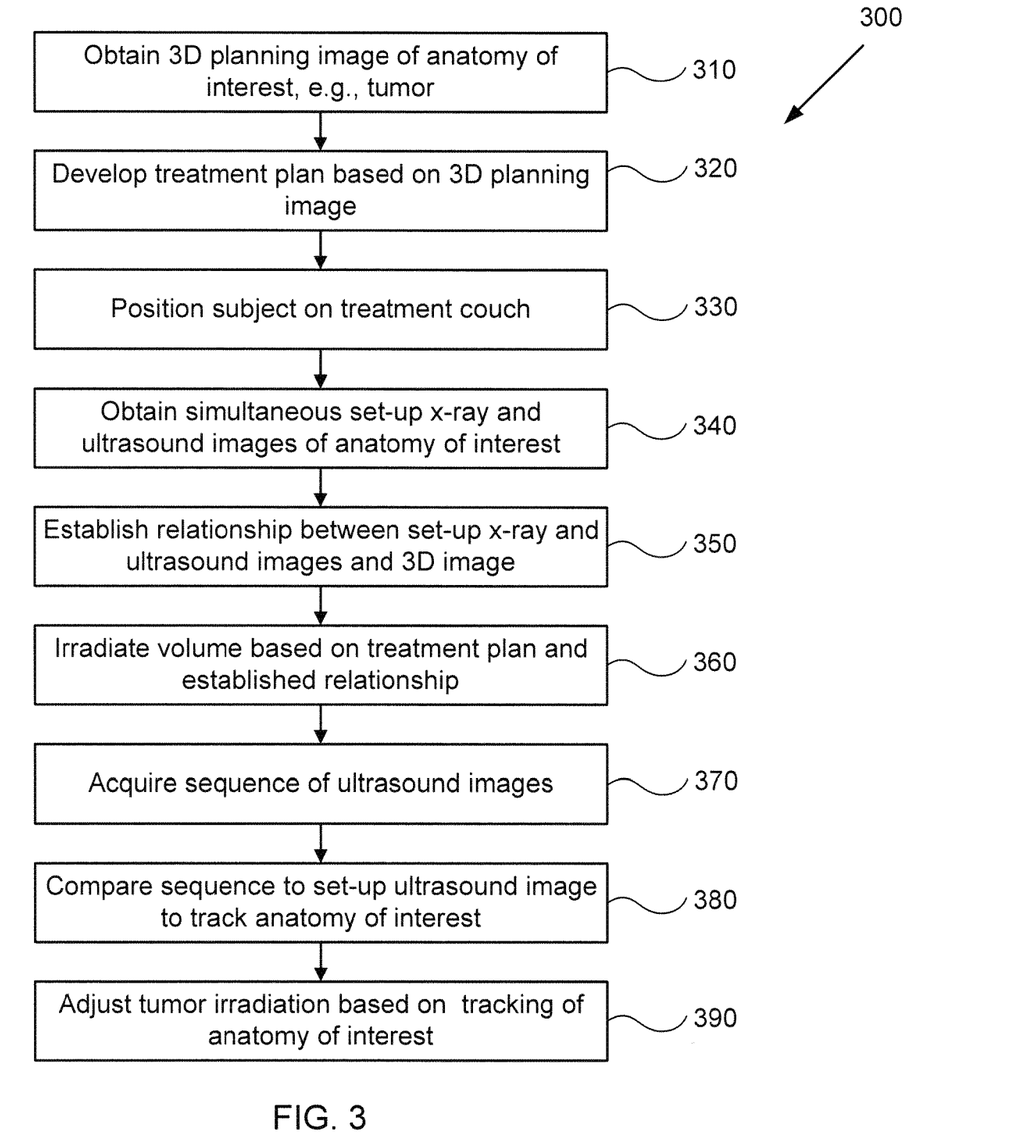
FIG. 3 is a flow chart of steps in an exemplary method for tracking a target volume.
Figure 4:
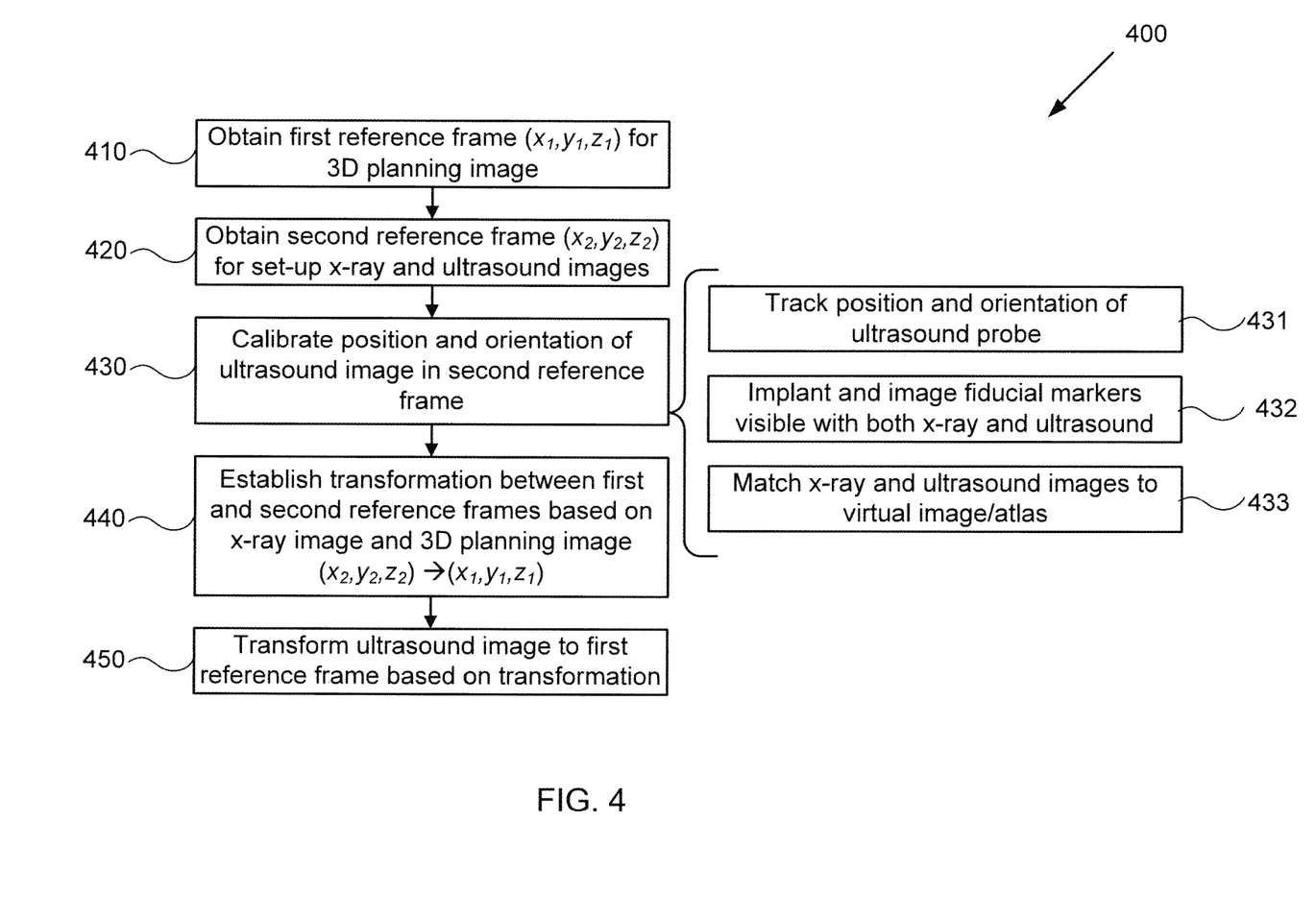
FIG. 4 is a flow chart of steps in an exemplary method for registering an ultrasound image to a high-resolution radiation treatment planning image.

FIG. 3 illustrates steps in a method 300 for using system 200 to track a target volume during a radiation treatment procedure. FIG. 4, described further below, provides enhanced detail for certain steps of method 300. The skilled artisan will readily appreciate modifications that may be made to the methods of FIGS. 3 and 4 for use with other types of radiation treatment systems, such as the gantry-based system illustrated in FIG. 5 and described in greater detail below.

Referring to FIG. 3, method 300 includes first obtaining a 3D image of a target volume, e.g., a tumor (step 310), to be used for planning the radiation treatment. The 3D planning image may be obtained using CT, MM, PET, or any other suitable imaging equipment.

A physician then develops a treatment plan based on the 3D planning image, also referred to as 3D planning image data (step 320). Such a plan may be developed using suitable commercially available software, such as mentioned above, which accepts and uses physician input as appropriate. Developing such a plan may include, for example, delineating the target volume as well as any nearby critical structures. Developing the treatment plan also includes defining a frame of reference for the 3D planning image, for example by selecting a point in the image to be the "origin" and determining a coordinate system for other points in that image with reference to that origin. Such an origin may be selected arbitrarily, or may be based on a particular feature in the image, e.g., the center of the target volume, or a particular physical feature represented in the image. The radiation doses, directions, and field sizes for the various fractions are determined with reference to the origin defined in the 3D planning image. The treatment plan may be developed using equipment other than that of system 200, and then transferred to controller 250 for storage in computer-readable medium 252. The 3D planning image is also transferred to controller 250 for storage in computer-readable medium 252.

After the treatment plan is developed and the patient otherwise prepared for the radiation treatment, the patient is positioned on the treatment couch 211 (step 330). If needed, controller 250 may issue instructions to robot-based support system 210 (or other suitable system) to move the treatment couch 211 using robotic arm 212, track 214, and/or column 215 so as to position the patient within the treatment room reference frame to coarsely align the reference frame of the 3D planning image with the treatment room reference frame, after which fine alignment may be performed using x-ray imaging sources 231, detectors 232, and ultrasound probe 240.

With the patient coarsely positioned, system 200 then substantially simultaneously obtains set-up x-ray and ultrasound images of anatomy of interest (step 340). By "substantially simultaneous" it is meant that the images are acquired within a time frame during which the anatomy of interest does not significantly move. For example, the x-ray and ultrasound images may be obtained within 100 milliseconds of one another, or within 50 milliseconds of one another, or within 20 milliseconds of one another, or within 10 milliseconds of one another, or within 5 milliseconds of one another, or even within 2 milliseconds of one another.

In one example, based on instructions stored in medium 252, processor 251 instructs x-ray imaging sources 231 and detectors 232 to obtain a pair of stereoscopic x-ray images of the target volume at substantially the same time that it instructs ultrasound probe 240 to obtain a 3D ultrasound image of the target volume. As will be appreciated, processor 252 stores the location and orientation of the ultrasound image in the treatment room reference frame, because the location and orientation of ultrasound probe 240 and the location and orientation of images produced by the probe have been calibrated within the treatment room reference frame, as described in greater detail below. However, the 3D planning image and the ultrasound image may differ significantly in appearance from one another because the two imaging modalities are sensitive to different tissue characteristics, and the images are typically obtained from different perspectives, thus making direct registration of the ultrasound image with the planning image a relatively difficult problem. After the images are obtained, detectors 232 and ultrasound probe 240 provide the respective set-up images to controller 250, which stores them in computer-readable medium 252.

A relationship between the set-up x-ray and ultrasound images and the 3D planning image, is then established (step 350). For example, the set-up x-ray and ultrasound images are related to one another in a well-defined way because they are inherently registered with one another in the treatment room reference frame by virtue of being acquired at substantially the same time, and by virtue of a known transformation relating the geometry of the X-ray imaging system with that of the ultrasound probe 240. To accurately execute the treatment plan developed in step 320 based on the actual position of the target volume within the treatment room reference frame, a relationship between the treatment room reference frame (i.e., the reference frame of the x-ray and ultrasound images) and the reference frame (treatment planning origin) of the 3D planning image is established. However, it is a relatively difficult problem to directly register the ultrasound image to the 3D planning image, because the two imaging modalities measure different tissue characteristics. For example, 3D CT images contain information about the electron density of tissue, whereas ultrasound images contain information about differences in acoustic impedance between adjacent tissues.

By comparison, it can be relatively straightforward to determine a relationship between a pair of set-up stereoscopic x-ray images (or other x-ray based image) and a 3D planning CT image, because both imaging modalities contain information about the electron density of tissue. For example, some gantry-based systems, e.g., from Varian Medical Equipment (Palo Alto, Calif.), Siemens (New York, N.Y.), or Elekta (Stockholm, Sweden), obtain a 3D set-up image, e.g., a cone-beam CT, and directly register that 3D set-up image to a 3D planning CT, e.g., perform a 3D-3D registration of like images. Or, for example, in the exemplary robot-based system illustrated in FIG. 2, such as the CYBERKNIFE® system (Accuray Incorporated, Sunnyvale Calif.), a set of digitally reconstructed radiographs (DRRs) is generated from the planning CT image that simulate the target volume in a variety of positions and orientations as it would appear in a pair of stereoscopic x-ray images obtained with an in-room imaging system. Then, during patient set-up, the pair of stereoscopic x-ray images of the target volume in its actual treatment room position and orientation are obtained and registered to the DRRs. In this example, the DRR having the best registration (best match), within a preset tolerance, with the set-up stereoscopic x-rays is used to generate a transformation between the planning CT image reference frame and the treatment room reference frame. Processor 251 uses this transformation to adjust the position and orientation of LINAC 221 to accurately deliver the radiation treatment according to the treatment plan, or to adjust patient treatment couch 211 and iterate the procedure until the patient is properly aligned before commencing radiation delivery. For further details on the use of DRRs in executing a radiosurgical treatment plan, see U.S. Pat. Nos. 7,204,640, 7,684,647, U.S. Patent Publication No. 2005/ 0049478, U.S. Patent Publication No. 2008/0130825, and W. Kilby, J. R. Dooley, G. Kuduvalli, S. Sayeh, C. R.

Maurer, Jr. The CyberKnife® Robotic Radiosurgery System in 2010. Technology in Cancer Research and Treatment. 9(5): 433-452, 2010, the entire contents of each of which are incorporated by reference herein.

By using the registration between the planning CT and the set-up stereoscopic x-ray images, and the inherent registration between the set-up stereoscopic images and set-up ultrasound images, embodiments of the present invention enable the ultrasound image to be readily related to the planning CT image, as represented by step 350 and as described in greater detail below with reference to FIG. 4. In one embodiment, computer-readable medium 252 of system 200 stores the 3D (e.g., CT) planning image, the set-up stereoscopic image pair, the DRRs, and the set-up ultrasound image, and processor 251 obtains the images from the computer-readable medium and processes them so as to establish relationships or registrations between the images. Processor 251 then stores information about those relationships, e.g., transformations, in computer-readable medium 252, for future use.

Referring again to FIG. 3, following this set-up, processor 251, automatically or by order of a user, begins irradiation of the target volume according to the treatment plan using the registrations between the set-up x-ray and ultrasound images and the 3D planning image (step 360).

As mentioned above, the target volume may move during treatment, as will be appreciated by the skilled artisan. To track intrafraction target volume movement in real-time, a sequence of ultrasound images may be acquired while the treatment progresses (step 370), and these ultrasound images can be relatively easily registered to the set-up ultrasound image to track intrafraction tumor position, as described more fully below. For example, the ultrasound images may be acquired at a relatively high frame rate, e.g., between 1 Hz and 30 Hz, or at an even higher frame rate, or at any other desired frequency. The various images of the sequence may capture tissue motion that occurs on time frames comparable to the frame rate of the sequence.

The ultrasound images of the sequence are then registered to the set-up ultrasound image to determine the intrafraction position and/or orientation of the target volume (step 380). For example, displacements of the target volume between ultrasound images may appear as changes in intensity that processor 251 recognizes and uses to identify the new location and/or orientation of the target volume. Alternatively, displacements of another anatomy of interest, e.g., the diaphragm, may be used as surrogates to predict the position and/or orientation of the target volume. The irradiation of the target volume may then be adjusted based on this tracking (step 390), for example, by instructing robot-based LINAC 221 to adjust the angle, position, and/or field of the radiation being administered. Because the ultrasound images are acquired in "real-time," e.g., with a frequency that accurately captures target volume motion on time-frames of medical concern, and because the processor 251 can issue instructions to robot-based LINAC 221 that compensate for such motion on such time-frames, the accuracy of the radiation treatment is enhanced, and the risk of damage to otherwise healthy tissues is reduced. Note that the ultrasound images of the sequence can also, or alternatively, be compared to the planning 3D image such as an MR image, to a setup 3D image, e.g., a cone-beam CT or MR image, and/or to x-ray images obtained during the treatment process.

Further details of a method 400 for establishing a relationship between set-up x-ray and ultrasound images and a 3D planning image will now be described with reference to FIG. 4.

First, a first reference frame $(x_1, y_1, z_1)$ is obtained for the 3D planning image (step 410). An origin and reference frame for this image is typically defined during the treatment planning stage. For embodiments in which method 400 is implemented using system 200, information about the first reference frame may be stored with the 3D planning image in computer-readable medium 252 and obtained therefrom by processor 251 for use in establishing the relationships between the various images.

Then, a second reference frame $(x_2, y_2, z_2)$ is obtained for the set-up x-ray and ultrasound images (step 420). For example, the origin of the second reference frame may be arbitrarily defined as a point in the treatment room. Or, for example, the origin of the second reference frame may be defined as the location of physical object that exists in the treatment room during a calibration step. The positions and orientations of robot-based support system 210, robot-based LINAC system 220, x-ray imaging sources 231, and detectors 232 are typically fixed and/or controlled with respect to the origin of the second reference frame, enabling their coordinates in the second reference frame to readily be determined at any moment. For example, the line within the treatment room reference frame corresponding to a pixel in one of the stereoscopic x-ray images recorded by detectors 232 and provided to controller 250 (step 340 of FIG. 3) can readily be determined.

However, the actual position and orientation of ultrasound probe 240 with respect to the origin of the treatment room reference frame is not necessarily fixed or known a priori. Additionally, the set-up ultrasound image typically has a different view of the target volume than does the set-up x-ray image, because the ultrasound probe 240 views the target volume from a different angle and position than do the x-ray imaging sources 231 and detectors 232. Method 400 includes calibrating the position and orientation of the ultrasound image within the second reference frame $(x_2, y_2, z_2)$ (step 430).

Some embodiments include calibrating the position and orientation in the second reference frame of the ultrasound image by tracking the position and orientation of the ultrasound probe (step 431). The position and orientation of the ultrasound image relative to the ultrasound probe can readily be determined using techniques known in the art. If the position and orientation of the ultrasound probe is known within the second reference frame, then the position and orientation of the ultrasound image in the second reference frame also can readily be determined. However, if the probe subsequently moves within the second reference frame, it may be useful to periodically or continuously track the probe's movement so as to know the position and orientation of the ultrasound image within the second reference frame.

For example, system 200 may include a plurality of visible markers placed at suitable locations on ultrasound probe 240, and one or more optical cameras that have a view of ultrasound probe 240 and that are in operable communication with controller 250. During use, the optical camera(s) record images of the visible markers on probe 240, and provides the images to controller 250. Based on these images, controller 250 determines the locations of the visible markers, and from this determines position and orientation of ultrasound probe 240 in the second reference frame, and uses this information to determine the position and orientation of the ultrasound image in the second reference frame. Advantageously, such an embodiment does not require the use of implanted fiducial markers into the subject. Examples of suitable visible markers include light emitting diodes (LEDs). Other suitable techniques for tracking the position and orientation of ultrasound probe 240 may alternatively be used, such as systems based on electromagnetic fields other than visible light, e.g., infrared light, RFID, or magnets. Other embodiments using fiducials implanted into the subject are described further below.

Method 400 further includes establishing a transformation between the first and second reference frames $(x_1, y_1, z_1)$ and $(x_2, y_2, z_2)$, based on the set-up x-ray image and the 3D planning image (step 440). Step 440 can be performed before, after, or concurrently with step 430. Step 440 may be performed using any suitable algorithm known in the art. For example, as noted above, the commercially available CYBERKNIFE® system establishes such a transformation by generating a set of DRRs based on the 3D planning image that simulate a range of views of the target volume that could possibly be obtained using x-ray imaging sources 231 and detectors 232. Then, based on a comparison of the actual set-up x-ray images to the DRRs and the known, fixed position of x-ray imaging sources 231 and detectors 232 within the second reference frame, the actual location and orientation of the target volume in the second reference frame $(x_2, y_2, z_2)$ can be determined and readily related to the first reference frame $(x_1, y_1, z_1)$. In such an embodiment, the DRRs may be pre-generated using a separate processor and stored in computer-readable medium 252 for use by processor 251 as appropriate. Any other suitable technique for establishing a transformation between the first and second reference frames may be used, such as known in the art.

Based on the transformation established in step 440, information from the set-up ultrasound image may then be referred into the first reference frame $(x_1, y_1, z_1)$ (step 450). The transformation established in step 440 may further be applied to any subsequently obtained ultrasound images, e.g., the sequence of images obtained while irradiating the target volume (step 370 of FIG. 3), and the irradiation adjusted as appropriate to compensate for target volume motion (step 390 of FIG. 3). The irradiation may be adjusted using the 3D planning image and updated information about the target's location, which is readily relatable to the 3D planning image through the step 440 transformation applied to a recently acquired ultrasound image.

Further details of different components of system 200 and of the methods that may be implemented using system 200, and some examples of alternative embodiments, will now be provided.

Ultrasound Probe Tracking

Other embodiments for registration of the set-up ultrasound image in the second reference frame (step 430) to the planning image include using fiducial markers that are implanted in or near the target volume and that are visible both in the x-ray and ultrasound images (step 432). In this embodiment the set-up ultrasound image of the target volume can be registered directly to the planning image by use of the fiducials visible in both imaging modalities. Intrafraction ultrasound images can then be registered back to the set-up ultrasound image that has been registered to the planning image, or the intrafraction ultrasound image can be directly registered to the planning image, the former being preferred. This registration is possible because the position and orientation of each fiducial marker in the x-ray image can readily be related to the position and orientation of the same fiducial marker in the ultrasound image, using known image analysis algorithms or other suitable software. Examples of suitable fiducial markers include X-MARK™ and X-MARK ULTRA™ elongated fiducial markers, available from ONC Solutions (Acton, Mass.). In another embodiment, the ultrasound probe 240 is arranged such that it appears in the set-up x-ray images. The position and orientation of the ultrasound probe 240 in the x-ray reference frame can be determined from the set-up x-ray images using the known geometry of the ultrasound probe, known image analysis algorithms and other suitable software.

In still another embodiment, the location and orientation of the ultrasound image in the second reference frame is calibrated based on a virtual image pair (step 433). By "virtual image pair" it is meant a pair of atlases, e.g., pre-existing images of an arbitrary patient having substantially normal anatomy in terms of relative position and shape of structure, or of an averaged image of multiple patients. Preferably, the atlases will consist of a first atlas of the same modality as the planning 3D image, and a second, 3D ultrasound atlas, with a known correspondence between each point in the first and second atlases. The first and second atlases may be stored in computer-readable medium 252. Controller 250 may register the planning CT image to the CT atlas using a first transformation; may register the set-up stereoscopic x-ray images to the CT atlas or the planning 3D image using a second transformation; and may register the set-up ultrasound image to the ultrasound atlas using a third transformation. The first, second, and third transformations then may be used to register the planning CT, set-up stereoscopic x-ray, and ultrasound images to one another. For further details on image registration using virtual images, see U.S. Patent Publication No. 2007/0038058, the entire contents of which are incorporated by reference herein.

Treatment Planning

Figure 5:
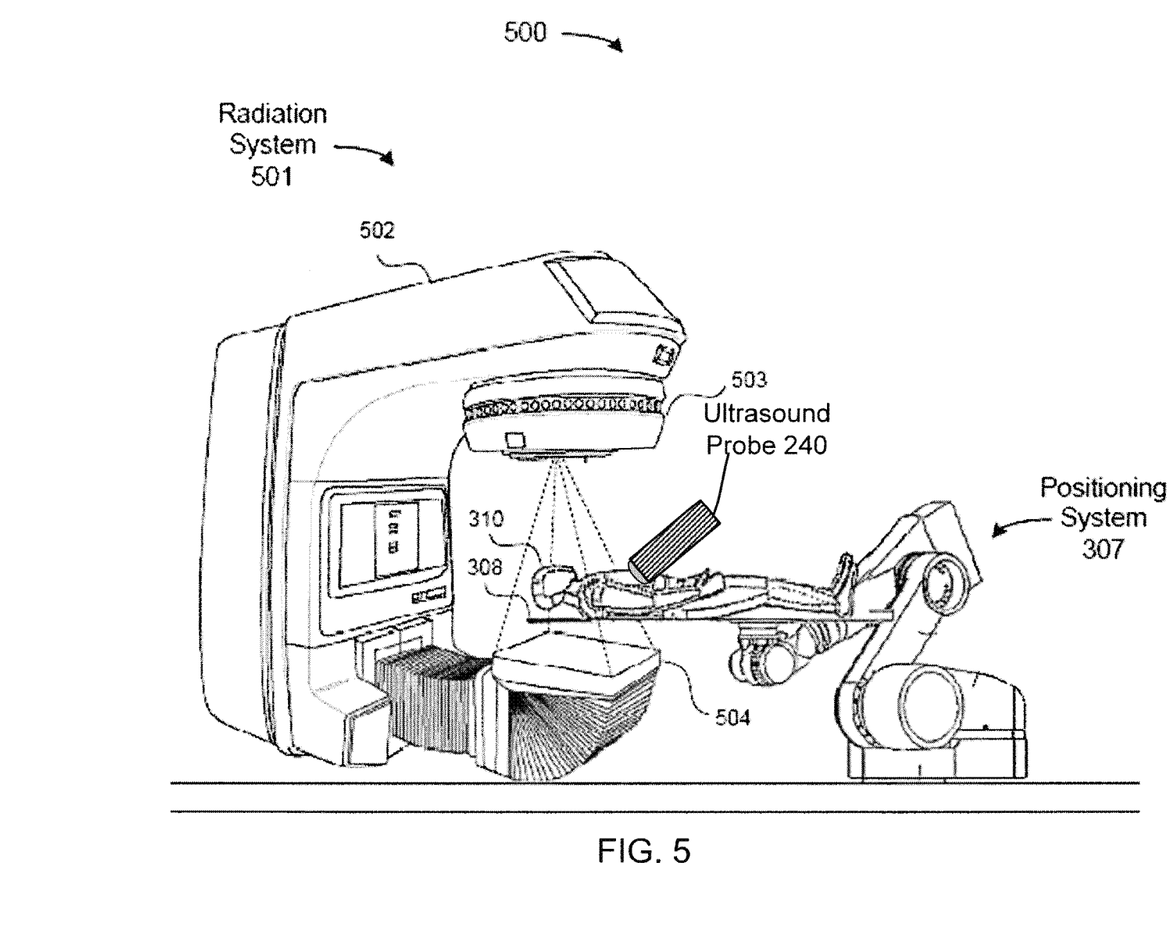
FIG. 5 schematically illustrates a perspective view of a gantry-based radiation treatment system having an ultrasound probe for tracking a target volume.
Figure 6:
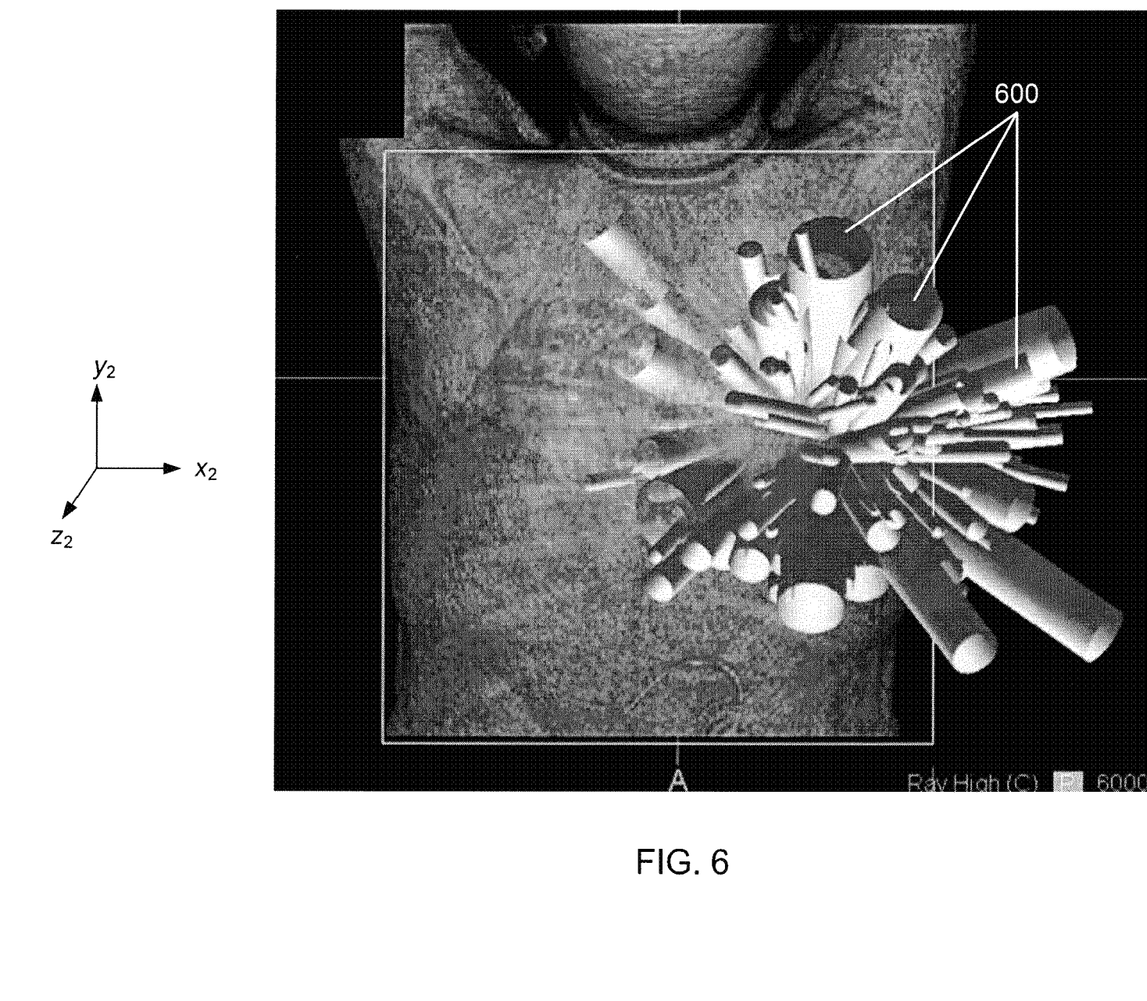
FIG. 6 is a perspective view of a radiosurgical treatment plan.

The treatment of a target volume (e.g., a tumor) may be planned (step 320 of FIG. 3) using hardware and software external to system 200 based on one or more previously obtained 3D images, e.g., volumetric CT images (step 310 of FIG. 3). The 3D images allow the target volume and nearby organs at risk (OARs) to be visualized. Once acquired, the 3D images are transferred to a computer system configured to perform treatment planning. In one exemplary embodiment, the computer system is a MULTIPLAN® treatment planning system (Accuray Incorporated, Sunnyvale, Calif.). In another exemplary embodiment, the computer system is an Eclipse® treatment planning system (Varian Medical Systems, Palo Alto, Calif.). Using such a system, a plurality of treatment fractions that appropriately irradiate the target volume are planned with reference to a first reference frame $(x_1, y_1, z_1)$. For example, each fraction may be described by a vector linking a source point and a direction point. The source point is the position of the LINAC focal spot. The direction point is usually within the target volume defined by the physician using the imaging datasets. Each source point is defined to be a node and the complete set of nodes defined to be a path set. Where the treatment plan is to be delivered using a robot-based radiation therapy system, such as illustrated in FIG. 2, a subset of the path set is used. This subset provides a set of non-coplanar treatment fractions 600, as depicted in FIG. 6. In such embodiments, all non-coplanar fractions may be administered without moving the patient, but instead by moving the LINAC, e.g., using robotic arm 222 illustrated in FIG. 2. The appropriate path set for each patient may be selected manually at the start of the treatment planning process. Alternatively, where the treatment plan is to be delivered using a gantry-based radiation therapy system, such as illustrated in FIG. 5 described further below, a variety of gantry angles and collimator leaf positions is used to provide a set of coplanar treatment fractions. If the gantry-based treatment is an IMRT (Intensity Modulated Radiation Therapy) treatment, the collimator leaf positions are changed while the gantry is at each angle in order to optimize the radiation dose distribution to the target.

Direction points may be determined automatically based on the beam generation mode, which the physician may select to be either isocentric or non-isocentric. The isocentric mode allows the physician to position one or more pseudo-isocenters within the patient model, resulting in one candidate beam from each node to each pseudo-isocenter. The non-isocentric mode takes advantage of the ability of the robotic manipulator to direct each beam at a unique point within the patient, without any need to reposition the patient between beams, by generating a large number of direction points (typically 1,000-6,000) semi-randomly within the target volume and distributing these points uniformly among the nodes to form a candidate beam set. The physician can choose to prevent candidate beams from passing through organs at risk (OARs), which can reduce the dose delivered to those organs. Such a feature can be particularly useful when the OARs are small radiosensitive structures such as the lens of the eye or the thyroid gland.

The physician also selects among a variety of suitable sizes of LINAC collimators that are assigned to subsets of the candidate beam set. As will be familiar to those skilled in the art, LINAC collimators may be used adjust the radiation fields of the various fractions as appropriate. FIG. 6 illustrates the different radiation fields of fractions 600 as cylinders of different diameters, where larger diameters correspond to larger fields, and larger collimators. The isocentric mode produces dose distributions including approximately spherical dose clouds around each pseudo-isocenter similar to those in other radiation treatment systems using circular collimators. The non-isocentric mode provides a different treatment geometry which is more similar to those achieved using multiple pencil beams. From a single node, a modulated fluence pattern can be delivered using multiple beams directed at unique points within the target volume, each of which has an independent radiation field and dose, as illustrated in FIG. 6. The radiation dose to be delivered in each fraction 600, represented by the length of fraction 600, may be obtained by inverse planning methods known in the art.

The thus-prepared treatment plan includes the position and orientation of each treatment fraction in a stereotactic coordinate system defined by the target anatomy itself or an internal surrogate fixed relative to it (i.e., in target space), together with the field size and dose to be delivered with each fraction. This information is stored as part of a treatment plan and is transferred to computer-readable medium 152 of the treatment delivery system 200 via an appropriate communication link.

Controller 250

As noted above with reference to FIG. 2, controller 250 may determine the beam alignment at the time of treatment based on automatic registration of digitally reconstructed radiographs (DRRs) generated from the 3D patient model, with live images acquired using the x-ray imaging sources 231 and detectors 232 of treatment system 100. In some embodiments, this results in two independent transformations, one for each of the live image and DRR pairs, which are combined and converted into a 3D transformation by, for example, geometric backprojection, a technique known in the art. Because the positions and orientations of x-ray imaging sources 231 and detectors 232 in second reference frame $(x_2, y_2, z_2)$ are known, controller 250 can readily determine the transformation between the first reference frame $(x_1, y_1, z_1)$ and the second reference frame can readily using techniques known in the art. This transformation allows the position and orientation of each treatment fraction relative to the target volume that was simulated on the TPS to be achieved during treatment based on the actual position and orientation of the target volume. For further details on the use of DRRs in executing a radiosurgical treatment plan, see U.S. Pat. Nos. 7,204,640, 7,684,647, U.S. Patent Publication No. 2005/0049478, and U.S. Patent Publication No. 2008/0130825, the entire contents of each of which are incorporated by reference herein.

During treatment, the controller 250 moves in sequence through the nodes selected during treatment planning, and issues instructions as appropriate to robot-based support system 210 and robot-based LINAC system 220 to adjust the relative position of the LINAC and the patient (more below). An optimized path traversal algorithm allows the controller 250 to provide instructions for robotic systems 210, 220 to travel only between nodes at which one or more treatment beams are to be delivered, or through the minimum number of additional zero-dose nodes required to prevent the robots from intersecting fixed room obstacles or a 'safety zone' surrounding the couch 211 and patient. At each node, the controller provides instructions to robotic systems 210 and/or 220 to re-orient the LINAC relative to the patient such that any fractions originating at the node can be delivered.

Controller 250 issues instructions to ultrasound probe 240, x-ray imaging sources 231, and detectors 232 to acquire images of the target volume at appropriate frequencies during treatment; assesses motion of the target volume based on same; and issues additional instructions to robotic systems 210, 220 as appropriate to adjust the relative position of the LINAC and the patient. In some embodiments, the imaging interval can be adjusted during treatment based on the stability of the target position. Responsive to relatively large translations and/or rotations of the target volume, controller 250 may automatically pause the treatment and reposition the patient before proceeding.

Robot-Based Support System 210

Before beginning treatment, controller 250 of robot-based radiation therapy system 200 aligns the patient using an adjustable treatment table, e.g., robot-based support system 210 illustrated in FIG. 2. Any suitable adjustable table may be used. For example, both a five-axis table and a six-axis ROBOCOUCH® Patient Positioning System are commercially available (Accuray, Inc.). Another commercially available six-axis patient positioning system is Protura® (Civco Medical Solutions, Inc.) With the five-axis table a sixth adjustment (yaw angle) can be applied manually. The purpose of this initial alignment is to reduce the size of corrective movements by support system 210 to below maximum limits, which in some embodiments are ±10 mm or ±25 mm in each direction and ±1° to ±5° about each axis depending on the tracking mode, path set, and couch design. After the patient is aligned within these limits, controller 250 determines any additional translational and rotational corrections needed to precisely align each treatment fraction with the target volume. The controller 250 provides these corrections to robot-based support system 210. During treatment, fine alignment of the treatment fractions preferably is achieved by adjusting the fraction position and orientation using robot-based LINAC system 220 relative to the patient, instead of adjusting the position of the patient relative to the fraction.

Robot-Based LINAC System 220

In some embodiments, LINAC 221 illustrated in FIG. 2 includes an X-band cavity magnetron and a standing wave, side-coupled accelerating waveguide, to produce a 6 MV X-ray treatment beam with a dose-rate of 1000 cGy/min. The compact design allows a configuration that does not require a bending magnet or a beam flattening filter. Secondary collimation may be provided using twelve fixed circular collimators with diameters ranging from 0.5-6 cm. These collimators can be fitted manually or automatically, for example using the commercially available XCHANGE® Robotic Collimator Changer (Accuray, Inc.). Alternatively, the commercially available IRIS® Variable Aperture Collimator (Accuray, Inc.) allows the same set of twelve field sizes to be achieved with a single variable aperture, and therefore provides the flexibility to apply any field size at any beam position without the need to swap collimators during treatment.

LINAC 221 is mounted on robotic arm 222, which in one illustrative embodiment is a KR240-2 (Series 2000) robotic manipulator (Kuka Roboter GmbH, Augsburg, Germany) that has a manufacturer specification for position repeatability of better than 0.12 mm, and has six degrees of freedom, thus allowing it to position the LINAC 221 within a large 3D workspace around the patient with high precision. The robotic arm 222 allows each treatment beam to be directed at a unique point in space and also removes any coplanar constraint on the beam geometry. This geometric flexibility means that the room or vault in which system 200 is installed requires a larger primary barrier than is typical for a gantry-mounted LINAC such as illustrated in FIG. 5 described below, because the beam directions are much less constrained. Optionally, system 200 can be installed in a 'gantry vault' configuration in which controller 250 restricts the beam directions to respect the limitations of a conventional vault primary barrier on the side walls, with the option of allowing additional beams incident on the inferior wall if this is adequately shielded.

As noted above, controller 250 preferably issues instructions to robot-based LINAC system 220 during treatment to compensate for changes in target position and orientation, e.g., to adjust the position and orientation of each treatment fraction, instead of moving the patient, which may provide enhanced alignment accuracy.

X-Ray Imaging Sources 231 and Detectors 232

As illustrated in FIG. 2, x-ray imaging sources 231 are mounted to the ceiling in which robot-based radiation treatment system 200 is located, and are configured to illuminate two corresponding x-ray detectors 232. In one illustrative embodiment, sources 231 each project x-ray fields at 45° from vertical, e.g., are positioned orthogonally to one another, and support a range of energies up to 150 kVp. At the point where the central axes of the beams generated by sources 131 intersect, the x-ray field size is approximately 15×15 cm. Detectors 232 are flat-panel x-ray detectors, which may be mounted on angled supports as illustrated or instead may be mounted flush with the floor. Detectors 232 include cesium-iodide scintillator deposited directly on amorphous silicon photodiodes, and are configured to generate high-resolution digital images (1,024×1,024 pixels with 16-bit resolution). Preferably, the x-ray imaging sources 231 and detectors 232 are rigidly fixed, and their projection geometry is calibrated and known with respect to the delivery system. Controller 250 may apply suitable software corrections to remove any distortions associated with the 45° angle between each detector and the imaging beam central axis.

Note that imaging systems other than x-ray imaging sources 231 and detectors 232 can be used to obtain images of the target volume that can be registered to the planning 3D image. For example, imaging systems for obtaining cone-beam CT images, PET images, SPECT images, tomosynthesis images, or in-room MR images can alternatively be used. Such systems are known in the art and can readily be adapted for use with the remainder of system 200. Such systems are particularly suitable for use in gantry-based embodiments such as illustrated in FIG. 5, described below.

Ultrasound Probe 240

Any suitable ultrasound probe 240 may be used to obtain ultrasound images of the target volume and provide those images to controller 250 for use in tracking the position and orientation of the target volume. Ultrasound probe 240 is preferably configured to obtain 3D images of the target volume, and may include, for example, a mechanically swept 1D ultrasound transducer array, or a 2D array with electronic beam steering that allows for fast volumetric imaging, e.g., with a frame rate of 25 Hz. Ultrasound probe 240 may be part of a commercially available 3D or 4D ultrasound system that is in operable communication with controller 250. Examples of suitable ultrasound systems include the iU22 and HD11 XE ultrasound systems (Koninklijke Philips Electronics N.V.) and the ACUSON S2000™ ultrasound system (Siemens AG, Malvern, Pa.).

Example

In one example, a radio-surgical procedure uses intrafractional ultrasound images to track movement of an anatomy of interest within a patient using system 200 of FIG. 2. The anatomy of interest may correspond to a target volume, e.g., a lesion, for irradiation by LINAC 221 or a structure within the patient that is fixed relative to the lesion. Prior to the procedure, a 3D planning image of the anatomy of interest patent is obtained using, e.g., a CT, MRI or other suitable imaging equipment. The 3D planning image is used by a physician to plan the procedure. After a treatment plan is developed, the planning image and treatment plan are accessible to controller 250 through the computer-readable medium 252.

The patient is placed on treatment couch 211 and aligned roughly with the reference frame adopted for the planning image, e.g., the geometric center of the lesion. Next, a transformation between the treatment room reference frame (the second reference frame) and the planning reference frame (the first reference frame) is determined by registering a DRR from the planning image with setup x-ray images generated by sources 231. Substantially simultaneously with acquisition of the setup x-ray images an ultrasound setup image is acquired using ultrasound probe 240. Since the x-ray and ultrasound images are acquired substantially simultaneously, they will be inherently similar to each other, i.e., the size, position and orientation of the lesion relative to other anatomy will be the same in both images. At the same time as these setup images are acquired, the location and orientation of the ultrasound probe 240 is also determined using an optical tracking device within the treatment room. With the location and orientation of the probe 240 known through this tracking device, therefore, a transformation between the ultrasound image reference frame and x-ray reference frame is also known. At this point, the transforms have been determined that allows a processor 251 of controller 250 to efficiently communicate information about the lesion's intrafractional position and shape from an ultrasound image in the planning image coordinates, in the event adjustments to the irradiation plan are needed to account for lesion motion within the body.

Thus, according to this example, an acquired intrafractional ultrasound image is related back to the planning image by processor 251 of the controller 250 in the following manner: (a) the intrafractional ultrasound image is transformed into the second reference frame using data received from the tracking device, (b) the transformed intrafractional ultrasound image is registered with the setup ultrasound image using any suitable known image registration algorithm, to detect a change in position, if any, of the lesion relative to the setup image, (c) a detected change in position is transformed into x-ray image coordinates based on the ultrasound setup image inherent registration (referring to the Ultrasound and x-ray images that were acquired substantially simultaneously to produce images of the anatomy that are inherently similar to each other) with the x-ray setup images, (d) then the change in position is transformed back to the planning image coordinates using the setup x-ray registration with the DRR.

Gantry-Based Embodiment

As noted above, the systems and methods of the present invention are also compatible with radiation treatment systems other than the robot-based system 200 illustrated in FIG. 2. For example, FIG. 5 schematically illustrates a gantry-based system 500. System 500 includes patient positioning system 307, gantry-based radiation system 501, and ultrasound probe 240 which may be substantially the same as ultrasound probe 240 described above with respect to FIG. 2.

Gantry-based radiation system 501 includes a gantry 502, a radiation source (e.g., LINAC) 503, and a portal imaging device 504. Gantry 502 is configured to move LINAC 503 in a fixed plane about the patient 310. LINAC 503 may include a multi-leaf collimator. Patient positioning system 307 may be a robotic system for moving patient 310 relative to the gantry 502, as shown, or any other suitable patient support system as known to the skilled artisan. Gantry-based radiation system 510, patient positioning system 307, and ultrasound probe 240 are in operable communication with a controller (not shown) that may be substantially the same as controller 250 described above with respect to FIG. 2, with suitable modifications made for operation with the particular radiation system and patient positioning system being used.

Patient set-up and tracking of a target volume may be performed using system 500 analogously to the patient set-up and target volume tracking described above with respect to FIGS. 2-4. For example, gantry-based system 500 is configured to obtain a cone-beam CT image of the target volume using LINAC 503 and portal imaging device 504 during patient set-up, at substantially the same time that it obtains an ultrasound image of the target volume using ultrasound probe 240. As for the stereoscopic pair of x-ray images described above, the set-up cone-beam CT image may be registered with the set-up ultrasound image, for example by tracking the ultrasound probe. The controller (not shown) registers the set-up cone-beam CT image to a previously obtained 3D CT planning image using techniques known in the art. The location and orientation of the ultrasound probe 240 in the treatment room are known from calibration, for example using any of the techniques described above with respect to FIG. 4. The controller then uses the set-up ultrasound image as discussed above to track intrafraction target motion. Radiation treatment then may be performed in accordance with the treatment plan, during which a plurality of intrafraction ultrasound images may be obtained. As described above with reference to FIGS. 3-4, those intrafraction images may be registered to the set-up ultrasound image, and used to track and compensate for motion of the target volume.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A method of tracking an anatomy of interest, the method comprising:
   receiving, from an ultrasound probe, a set-up ultrasound image of the anatomy of interest in a second reference frame;
   establishing a transformation between a first reference frame and the second reference frame by registering the set-up ultrasound image directly with a pre-acquired 3D image of the anatomy of interest;
   receiving, from the ultrasound probe, an intrafraction ultrasound image of the anatomy of interest;
   registering, by a processor, the intrafraction ultrasound image with the set-up ultrasound image; and
   tracking motion of the anatomy of interest based on the registered intrafraction ultrasound image.

2. The method of claim 1, wherein the pre-acquired 3D image comprises an MR image.

3. The method of claim 1, further comprising:
   determining a position and orientation of the set-up ultrasound image in the second reference frame by receiving, from a tracking device, positional data about markers affixed to the ultrasound probe; and
   identifying a position and orientation of the ultrasound probe in the second reference frame based on the positional data.

4. The method of claim 1, further comprising adjusting a position and orientation of a radiation source based on the tracked motion of the anatomy of interest.

5. The method of claim 1, further comprising adjusting a position and orientation of a patient treatment couch relative to a radiation source based on the tracked motion of the anatomy of interest.

6. The method of claim 1, further comprising enabling or disabling a treatment beam based on the tracked motion of the anatomy of interest.

7. The method of claim 1, further comprising adjusting a multileaf collimator to adjust delivery of a radiation treatment beam based on the tracked motion of the anatomy of interest.

8. The method of claim 1, wherein the pre-acquired 3D image is used to derive a treatment plan for irradiating a target volume associated with the anatomy of interest.

9. A system for tracking an anatomy of interest, the system comprising:
   a memory to store a pre-acquired 3D image of the anatomy of interest in a first reference frame; and
   a processor, operatively coupled with the memory, to:

receive, from an ultrasound probe, a set-up ultrasound image of the anatomy of interest in a second reference frame;

establish a transformation between the first reference frame and the second reference frame by registering the set-up ultrasound image directly with the pre-acquired 3D image of the anatomy of interest;

receive, from the ultrasound probe, an intrafraction ultrasound image of the anatomy of interest;

register the intrafraction ultrasound image with the set-up ultrasound image; and track motion of the anatomy of interest based on the registered intrafraction ultrasound image.

10. The system of claim 9, further comprising the ultrasound probe.

11. The system of claim 9, wherein the pre-acquired 3D image comprises an MR image.

12. The system of claim 9, the processor further to:
determine a position and orientation of the set-up ultrasound image in the second reference frame by receiving, from a tracking device, positional data about markers affixed to the ultrasound probe; and
identify a position and orientation of the ultrasound probe in the second reference frame based on the positional data.

13. The system of claim 9, the processor further to adjust a position and orientation of a radiation source based on the tracked motion of the anatomy of interest.

14. The system of claim 9, the processor further to adjust a position and orientation of a patient treatment couch relative to a radiation source based on the tracked motion of the anatomy of interest.

15. The system of claim 9, the processor to enable or disable a treatment beam based on the tracked motion of the anatomy of interest.

16. The system of claim 9, the processor further to adjust a multileaf collimator to adjust delivery of a radiation beam based on the tracked motion of the anatomy of interest.

17. The system of claim 9, wherein the pre-acquired 3D image is used to derive a treatment plan for irradiating a target volume associated with the anatomy of interest.

18. A non-transitory computer readable medium that, when executed by a processor, cause the processor to:
receive, from an ultrasound probe, a set-up ultrasound image of an anatomy of interest in a second reference frame;

establish a transformation between a first reference frame and the second reference frame by registering the set-up ultrasound image directly with a pre-acquired 3D image of the anatomy of interest;

receive, from the ultrasound probe, an intrafraction ultrasound image of the anatomy of interest;

register, by the processor, the intrafraction ultrasound image with the set-up ultrasound image; and track motion of the anatomy of interest based on the registered intrafraction ultrasound image.

19. The non-transitory computer readable medium of claim 18, wherein the pre-acquired 3D image comprises an MR image.

20. The non-transitory computer readable medium of claim 18, wherein the processor further to:
determine a position and orientation of the set-up ultrasound image in the second reference frame by receiving, from a tracking device, positional data about markers affixed to the ultrasound probe; and
identify a position and orientation of the ultrasound probe in the second reference frame based on the positional data.

21. The non-transitory computer readable medium of claim 18, wherein the processor further to adjust a position and orientation of a radiation source based on the tracked motion of the anatomy of interest.

22. The non-transitory computer readable medium of claim 18, wherein the processor further to adjust a position and orientation of a patient treatment couch relative to a radiation source based on the tracked motion of the anatomy of interest.

23. The non-transitory computer readable medium of claim 18, wherein the processor to enable or disable a treatment beam based on the tracked motion of the anatomy of interest.

24. The non-transitory computer readable medium of claim 18, wherein the processor further to adjust a multileaf collimator to adjust delivery of a radiation beam based on the tracked motion of the anatomy of interest.

25. The non-transitory computer readable medium of claim 18, wherein the pre-acquired 3D image is used to derive a treatment plan for irradiating a target volume associated with the anatomy of interest.

* * * * *